United States Patent [19]

Myers

[11] 4,133,950

[45] Jan. 9, 1979

[54] 4"-DEOXY-4"-CARBAMATE AND DITHIOCARBAMATE DERIVATIVES OF OLEANDOMYCIN AND ITS ESTERS

[75] Inventor: Robert F. Myers, East Lyme, Conn.

[73] Assignee: Pfizer Inc., New York, N.Y.

[21] Appl. No.: 866,891

[22] Filed: Jan. 3, 1978

[51] Int. Cl.$^2$ .................... C07H 17/08; A01N 9/00
[52] U.S. Cl. ............................ 536/9; 536/17; 424/180
[58] Field of Search .................... 536/9, 17; 424/180

[56] References Cited

U.S. PATENT DOCUMENTS

| | | | |
|---|---|---|---|
| 3,869,445 | 3/1975 | Hallas et al. | 536/9 |
| 3,884,903 | 5/1975 | Jones et al. | 536/9 |
| 3,884,904 | 5/1975 | Jones et al. | 536/9 |
| 4,063,014 | 12/1977 | Hallas et al. | 536/9 |
| 4,069,379 | 1/1978 | Sciavolino | 536/9 |

*Primary Examiner*—Johnnie R. Brown
*Assistant Examiner*—Blondel Hazel
*Attorney, Agent, or Firm*—Francis X. Murphy; Charles J. Knuth; Albert E. Frost

[57] ABSTRACT

Derivatives of oleandomycin, its 11-monoalkanoyl and 11,2'-dialkanoyl esters having at the 4"-position an amino group substituted with —C(=X)—X—$R_3$ wherein X is O or S and $R_3$ is alkyl, phenyl or benzyl groups, each of which may be substituted or unsubstituted, or a pyridylmethyl group, their preparation and use as antibacterial agents is described.

11 Claims, No Drawings

4"-DEOXY-4"-CARBAMATE AND DITHIOCARBAMATE DERIVATIVES OF OLEANDOMYCIN AND ITS ESTERS

BACKGROUND OF THE INVENTION

1. Field of the Invention

This invention relates to a structurally unique group of macrolides and, more particularly, to derivatives of oleandomycin, its 11-mono- and 11,2'-dialkanoyl esters having at the 4"-position an amino group substituted with —C(=X)—X—$R_3$ wherein X is O or S and $R_3$ is alkyl, phenyl or benzyl groups each of which may be substituted or unsubstituted, or a pyridylmethyl group, and to methods for their preparation. The compounds are antibacterial agents.

2. Description of the Prior Art

Oleandomycin, a macrolide antibiotic produced by fermentation, was first described in U.S. Pat. No. 2,757,123. It has the formula, the absolute configuration of which is shown below:

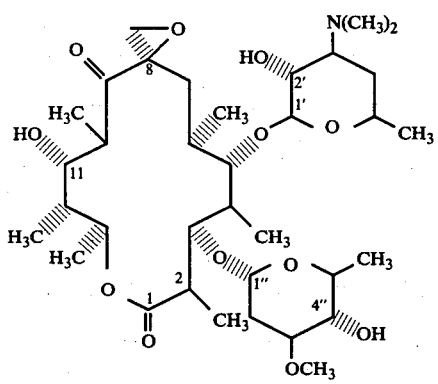

It consists of three main structural features: the L-oleandrose moiety, the desosamine moiety and the oleandolide moiety.

Derivatization of oleandomycin has focused primarily upon the formation of esters at one or more of three hydroxy groups located at the 2', 4" and 11-positions. Mono-, di and triacyl esters wherein the acyl moiety is derived from a lower aliphatic hydrocarbon monocarboxylic acid having from two to six carbon atoms are described in U.S. Pat. No. 3,022,219.

Aminohydrin derivatives of oleandomycin are reported by Kastrons et al., *Khim. Geterosikl Soedin* (2), 168–71 (1974); C.A. 80, 145986n (1974). The compounds, for which no utility is reported, are prepared by treating oleandomycin with a dialkylamine or a heterocyclic amine in a sealed tube for twenty hours at 30° C. The epoxide moiety at the 8-position is the site of reaction.

SUMMARY OF THE INVENTION

There has now been found a series of oleandomycin derivatives each of which exhibits valuable antibacterial activity in vitro and many of which exhibit in vivo activity by the parenteral and oral routes of administration, particularly against Gram-positive microorganisms. The compounds of this invention have formula II below wherein the wavy line connecting the substituted amino group at the 4"-position is generic to and embracive of both epimeric forms:

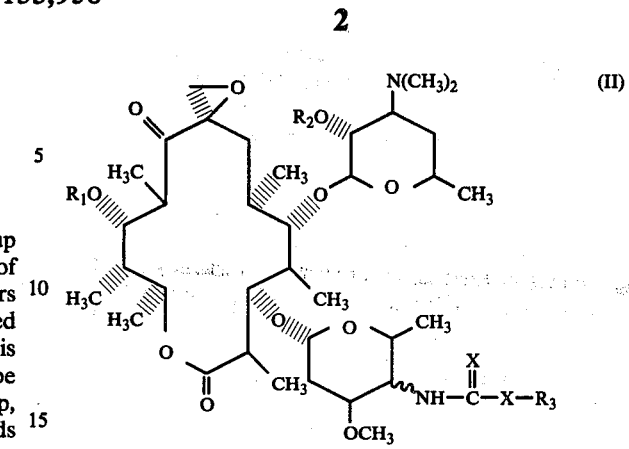

wherein each of $R_1$ and $R_2$ is selected from the group consisting of hydrogen and alkanoyl having from two to three carbon atoms;

X is selected from the group consisting of O and S;

$R_3$ is selected from the group consisting of (i) a first subgroup consisting of

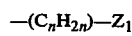

wherein $Z_1$ is selected from the group consisting of hydrogen, chloro, bromo, carboalkoxy having from one to four carbon atoms in the alkoxy group, hydroxy, alkoxy having from one to four carbon atoms and dimethylamino; n is an integer from 1 to 4;

with the provisos that when $Z_1$ is chloro, bromo, hydroxy or dimethylamino, n is an integer from 2 to 4; and when X is O, $Z_1$ is other than hydroxy or dimethylamino;

(ii) a second subgroup consisting of

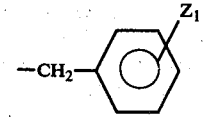

wherein $Z_1$ is as defined above;

(iii) a third subgroup consisting of

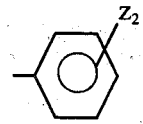

wherein $Z_2$ is selected from the group consisting of hydrogen, chloro, bromo, carboalkoxy having from one to four carbon atoms in the alkoxy group, alkoxy having from one to four carbon atoms and alkyl having from one to four carbon atoms; and, when X is S, (iv) a fourth subgroup consisting of

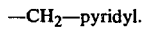

Also included in the present invention are the pharmaceutically acceptable salts of compounds of formula II above. Representative of such salts, but are limited thereto, are the hydrochloride, hydrobromide, phosphate, sulfate, formate, acetate, propionate, butyrate, citrate, glycolate, lactate, tartrate, maleate, fumatate, gluconate, stearate, mandelate, pamoate, benzoate, succinate, lactate, p-toluenesulfonate, and aspartate.

Favored because of their greater biological activity relative to that of other compounds described herein are compounds of formula II wherein $R_1$ is alkanoyl, $R_2$ is hydrogen, and X and $R_3$ have the values shown below:

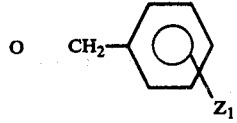

Preferred compounds are those wherein $R_1$ is acetyl; $R_2$ is hydrogen, and X and $R_3$ have the values shown below:

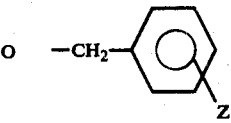

Compounds of formula II, including the epimeric forms thereof, and their pharmaceutically acceptable salts are effective antibacterial agents against Gram-positive microorganisms, e.g. *Staphylococcus aureus* and *Streptococcus pyogenes*, in vitro and many are active in vivo via the parenteral and oral routes of administration. Many of the compounds (and their salts) are also active against certain Gram-negative microorganisms, such as cocci, e.g. *Pasteurella multocida* and *Neisseria sicca*.

DETAILED DESCRIPTION OF THE INVENTION

The structurally unique oleandomycin derivatives of this invention of formula II are prepared by reaction of the appropriate amine of formula III:

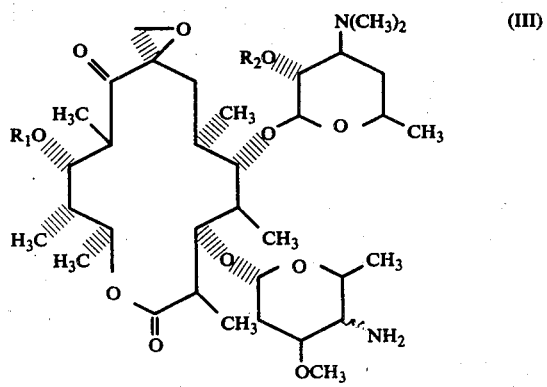

wherein each of $R_1$ and $R_2$ is as previously defined, with the appropriate acylating agent having the formula Cl—C(=X)X—$R_3$ in a reaction-inert solvent in the presence of an acid acceptor. An excess of the amine reactant of formula III can be used as the acid acceptor. Alternatively, a tertiary alkylamine, such as a trialkylamine having from 3 to 12 carbon atoms, and preferably triethylamine, or other commonly used tertiary organic bases such as pyridine, N,N-dimethylaniline or N-methylmorpholine, can be used as the acid acceptor.

The reaction is generally conducted in an inert atmosphere to avoid possible effects of atmospheric oxygen on the reactants.

The molar ratio of the Cl—C(=X)X—$R_3$ compound to amine reactant of formula III can vary widely, e.g. from about 1:1 to about 3:1. Molar ratios of less than 1:1 are avoided for economic reasons to insure maximum reaction of the amine reactant, normally the least readily available of the reactants. Ratios of greater than 3:1 are seldom used since they do not appear to improve the yield of the final product. The use of an acid acceptor other than the amine reactant of formula III itself affords satisfactory yields of product with the use of from about 1:1 to about 3:1 moles of amine reactant to the acylating agent. The reaction is essentially an acylation reaction.

Suitable reaction-inert solvents (i.e., those which do not react to any appreciable extent with the reactants or products) are the dimethyl ether of ethylene glycol, tetrahydrofuran, n-dibutylether, diethylether, toluene, acetonitrile, chloroform and methylene chloride. The principle criteria for the solvent are that it remain liquid at the relatively low temperatures at which the reaction is conducted and, of course, that it solubilize the reactants to an appreciable extent, if not completely.

The reaction is carried out at temperatures from about $-80°$ C. to about $-30°$ C. This temperature range affords a satisfactory rate of reaction and eliminates or minimizes side reactions.

An alternate procedure comprises reacting the amine reactant of formula III with the appropriate compound of formula Cl—C(=X)X—$R_3$ under Schotten-Baumann conditions well known to those skilled in the art. A favored procedure comprises conducting the reaction in aqueous acetone at pH of about 8 and at ambient temperature.

The necessary reactants having the formula Cl—C(=X)X—$R_3$, if not available or known in the literature, are conveniently prepared by known methods. When X is oxygen, the procedure comprises the reaction of phosgene with the appropriate hydroxylic compound having the formula HO—$R_3$. The reaction is generally carried out at temperatures of from about $0°-15°$ C. in an appropriate solvent such as benzene, toluene, tetrahydrofuran, dioxane, diethyl ether, in the presence of an acid acceptor such as those enumerated above. Similarly, when X is sulfur, the required compounds are prepared by the reaction of thiophosgene upon the appropriate thiol compound (HS—$R_3$) under conditions substantially the same as those described above. The products are isolated by known procedures.

An alternative procedure for preparing compounds of formula II wherein X is sulfur comprises reacting a compound having formula III with carbon disulfide and an appropriate halo (chloro or bromo) compound having formula halo-$R_3$ in a suitable reaction-inert solvent. Suitable solvents for this alternative process are those enumerated above for the acylation reaction.

This alternative process is also conducted at low temperatures, desirably at temperatures of from about −50° C. to about room temperature. The general procedure comprises adding carbon disulfide to a solution of the amino reactant of formula III in the presence of an acid acceptor at a temperature of about −50° C. followed by the addition of the halo reactant. Upon completion of addition of the halo reactant, the reaction mixture is generally allowed to gradually warm to about 0° C. to room temperature after which the product is isolated by work-up procedure described herein.

As noted above, an excess of the amino reactant of formula III can serve as acid acceptor in this alternative process. However, because of the relatively poor availability of the amino reactant, it is preferred to use a tertiary base such as trialkyl amine, quinoline, pyridine or other tertiary base as acid acceptor. The amine of formula III and the halo reactant (halo-$R_3$) are generally used in equimolar proportions. The acid acceptor is often used in excess.

This process is especially useful for preparing compounds wherein X is sulfur because of the lack of availability of dithioacid derivatives having formula Cl—C(=S)S—$R_3$.

Since the amine reactant of formula III is a mixture of epimers at C-4″, the above described reactions produce a mixture of epimers (represented by a wavy line is formual II compounds) which can be separated, if desired. Column chromatography of a chloroform solution of the crude product on silica gel and elution with appropriate solvents, e.g. chloroform-3% methanol, offers a convenient method for separating the epimers. In the present description and illustrations, it is understood that although the compounds are listed as 4″-substituted amino derivatives, both epimers and mixtures thereof are included. The use of a single C-4″ epimer of a reactant of formula III, of course, affords the corresponding acylated derivative.

Acid addition salts of the compounds of this invention are readily prepared by treating formula II compounds with at least an equimolar amount of the appropriate acid in a reaction-inert solvent for the formula II compound. When more than one basic amino group is present in a compound of formula II, the addition of sufficient acid to satisfy each basic group permits formation of poly acid salts. The acid addition salts are recovered by filtration if they are insoluble in the reaction-inert solvent, by precipitation, by addition of a non-solvent for said salt, or by evaporation of the solvent.

The 11-monoalkanoyl- and 11,2′-dialkanoyl-4″-deoxo-4″-amino-oleandomycin reactants (formula III) are prepared by reductive amination of the corresponding 11-monoalkanoyl-, 2′-monoalkanoyl- and 11,2′-dialkanoyl-4″-deoxo-4″-oxo-oleandomycins using palladium-on-charcoal, hydrogen and ammonium acetate in a suitable solvent ($CH_3OH$, i-$C_3H_7OH$). Alternatively, sodium cyanoborohydride can be used as reducing agent in place of palladium-on-charcoal and hydrogen. The de-esterified derivative is conveniently prepared by hydrolysis of the corresponding 2′-monoalkanoyl-4″-deoxo-4″-amino-oleandomycin.

The novel oleandomycin derivatives described herein exhibit in vitro activity against a variety of Gram-positive microorganisms and against certain Gram-negative microorganisms such as those of spherical or elliposidal shape (cocci). Their activity is readily demonstrated by in vitro tests against various microorganisms in a brain-heart infusion medium by the usual two-fold serial dilution technique. Their in vitro activity renders them useful for topical application in the form of ointments, creams and the like; for sterilization purposes, e.g. sickroom utensils; and as industrial antimicrobials, for example, in water treatment, slime control, paint and wood preservation.

For in vitro use, e.g. for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media; that is, media which have no harmful effect on the active ingredient. For such purposes, it will generally be acceptable to employ concentrations of active ingredients of from about 0.01 percent to about 10 percent by weight based on total composition.

Additionally, many compounds of this invention are active versus Gram-positive and certain Gram-negative microorganisms in vivo via the oral and/or parenteral routes of administration in animals, including man. Their in vivo activity is more limited as regards susceptible organisms and is determined by the usual procedure which comprises infecting mice of substantially uniform weight with the test organism and subsequently treating them orally or subcutaneously with the test compound. In practice, the mice, e.g. 10, are given an intraperitoneal inoculation of suitably diluted cultures containing approximately 1 to 10 times the $LD_{100}$ (the lowest concentration of organisms required to produce 100% deaths). Control tests are simultaneously run in which mice receive inoculum of lower dilutions as a check on possible variation in virulence of the test organism. The test compound is administered 0.5 hour post-inoculation, and is repeated 4, 24 and 48 hours later. Surviving mice are held for four days after the last treatment and the number of survivors is noted.

When used in vivo, these novel compounds can be administered orally or parenterally, e.g., by subcutaneous or intramuscular injection, at a dosage of from about 1 mg./kg. to about 200 mg./kg. of body weight per day. The favored dosage range is from about 5 mg./kg. to about 100 mg./kg. of body weight per day and the preferred range from about 5 mg./kg. to about 50 mg./kg. of body weight per day. Vehicles suitable for parenteral injection may be either aqueous such as water, isotonic saline, isotonic dextrose, Ringer's solution, or nonaqueous such as fatty oils of vegetable origin (cotton seed, peanut oil, corn, sesame), dimethylsulfoxide and other non-aqueous vehicles which will not interfere with therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents; for example, propylene glycol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition.

In the Examples presented herein, no effort was made to recover the maximum amount of product produced or to optimize the yield of a given product. The Examples are merely illustrative of the process and of the products obtainable thereby.

EXAMPLE 1

11-Acetyl-4"-deoxy-4"-(benzylthio-thiocarbonyl-)amino-oleandomycin

A solution of 11-acetyl-4"-deoxy-4"-oleandomycin (2.0 g., 2.75 mmol.) in tetrahydrofuran (15 ml.) in a round-bottom 3-neck flask fitted with magnetic stirrer, a calcium chloride drying tube and dropping funnel is cooled to $-50°$ C. The solution is stirred and triethylamine (0.4 ml., 2.8 mmol.) is added followed by carbon disulfide (0.25 ml., 4 mmol.). The mixture is stirred at $-50°$ C. for 10 minutes and then benzylbromide (0.33 ml., 2.75 mmol. is added. The cooling bath is removed and the mixture allowed to warm. After about one-half hour (temperature $\simeq 0°$ C.), the mixture is poured into diethyl ether (200 ml.). The small amount of white solid which precipitates is filtered off. The ether filtrate is concentrated under reduced pressure to a white foam. The foam is partitioned between chloroform and water (pH 3) and the phases separated. The chloroform phase is extracted again with fresh water (pH 5.5) and the phases separated. The chloroform phase is once again extracted with water (pH 8) and the phases separated. The chloroform phase is dried ($Na_2SO_4$) and concentrated under reduced pressure to a white foam (1.4 g.). The foam is chromatographed on silica gel (100 g.) using acetone as eluant. Fractions of 15 ml. each are collected. Fractions 17–26 are combined to give, after evaporation, 0.456 g. of a white foam (19% yield).

NMR (60 MHz) $\delta_{CDCl_3}^{TMS}$ (ppm): 7.38 (s, 5H), 4.55 (s, 2H), 3.48 (s, 3H), 2.68 (d, J=2, 2H), 2.33 (s, 6H), 2.11 (s, 3H).

Similarly, the following compounds are prepared from appropriate reactants.

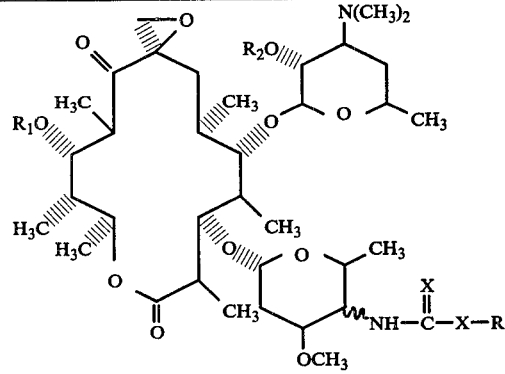

| R | R | X | $R_3$ |
|---|---|---|---|
| Ac | H | S | $n-C_4H_9$ |
| Pr | H | S | $i-C_3H_7$ |
| Ac | H | S | $CH_2CH_2OH$ |
| Ac | H | S | $(CH_2)_4OH$ |
| Pr | H | S | $CH_2CH(OH)C_2H_5$ |
| Pr | H | S | $CH_2CH_2Cl$ |
| Ac | Ac | S | $(CH_2)_3Br$ |
| Ac | H | S | $(CH_2)_4Cl$ |
| Ac | H | S | $CH(CH_3)CH(Br)CH_3$ |
| Ac | H | S | $CH_2CH_2OCH_3$ |
| Pr | H | S | $(CH_2)_2O-n-C_4H_9$ |
| Ac | Ac | S | $(CH_2)_4-OCH_3$ |
| Ac | H | S | $CH_2OCH_3$ |

-continued

| R | R | X | $R_3$ |
|---|---|---|---|
| Ac | H | S | $CH_2O-n-C_4H_9$ |
| Ac | H | S | $CH_2CH_2N(CH_3)_2$ |
| Ac | Pr | S | $(CH_2)_4N(CH_3)_2$ |
| Pr | Ac | S | $(CH_2)_3N(CH_3)_2$ |
| Ac | H | S | $CHCOOCH_3$ |
| Ac | Ac | S | $CH_2COO-n-C_4H_9$ |
| Pr | Pr | S | $(CH_2)_2COOCH_3$ |
| Pr | H | S | $(CH_2)_2COOC_3H_7$ |
| Ac | Ac | S | $(CH_2)_4COOCH_3$ |
| Ac | H | S | $CH_2)_4COO-n-C_4H_9$ |
| Ac | H | S | $CH_2C_6H_5$ |
| Ac | Ac | S | $CH_2-(4-CH_3C_6H_4)$ |
| Ac | H | S | $CH_2-(4-i-C_3H_7C_6H_4)$ |
| Pr | H | S | $CH_2-(4-t-C_4H_9C_6H_4)$ |
| Ac | H | S | $CH_2-3-ClC_6H_4$ |
| Ac | Pr | S | $CH_2-(3-CH_3OC_6H_4)$ |
| Ac | Ac | S | $CH_2-(3-C_4H_9OC_6H_4)$ |
| Pr | H | S | $CH_2$-2-pyridyl |
| Pr | H | S | $CH_2$-4-pyridyl |
| Ac | H | S | $2-CH_3OOCC_6H_4$ |
| Ac | H | S | $3-n-C_4H_9OOCC_6H_4$ |
| Pr | H | S | $CH_2-(4-CH_3OOCC_6H_4)$ |
| Ac | H | S | $CH_2-(3-C_3H_7OOCC_6H_4)$ |
| Ac | Ac | S | $CH_2$-2-pyridyl |
| Pr | Pr | S | $CH_2$-4-pyridyl |
| Pr | Ac | S | $CH_3$ |
| Pr | Pr | S | $CH_2C_2OH$ |
| Ac | Ac | S | $CH_2CH_2OH$ |
| H | Ac | S | $CH_3$ |
| H | Ac | S | $n-C_4H_9$ |
| H | Ac | S | $CH_2CH_2OH$ |
| H | Pr | S | $CH_2CH_2Cl$ |
| H | Pr | S | $(CH_2)_3Br$ |
| H | Pr | S | $CHCOOCH_3$ |
| H | Ac | S | $CH_2$-2-pyridyl |
| H | Ac | S | $CH_2—C_6H_5$ |
| H | Ac | S | $CH_2-(4-ClC_6H_4)$ |
| H | Ac | S | $CH_2-(2-CH_3C_6H_4)$ |
| H | Ac | S | $CH_2-(4-t-C_4H_9C_6H_4)$ |
| H | Pr | S | $CH_2-(4-C_2H_5OC_6H_4)$ |
| H | Pr | S | $CH_2$-2-pyridyl |
| H | H | S | $CH_3$ |
| H | H | S | $n-C_4H_9$ |
| H | H | S | $CH_2CH_2OH$ |
| H | H | S | $(CH_2)_3Cl$ |
| H | H | S | $CH_2CH_2OCH_3$ |
| H | H | S | $CH_2COOC_2H_5$ |
| H | H | S | $CH_2C_6H_5$ |
| H | H | S | $CH_2(4-ClC_6H_4)$ |
| H | H | S | $CH_2-(2-CH_3OOCC_6H_4)$ |
| H | H | S | $CH_2-(4-C_2H_5OC_6H_4)$ |
| Ac | H | S | $(CH_2)_3OH$ |
| Ac | Ac | S | $(CH_2)_4OH$ |
| Ac | H | S | $CH_2CH_2N(CH_3)_2$ |
| Pr | H | S | $(CH_2)_3N(CH_3)_2$ |
| Ac | H | S | $(CH_2)_4N(CH_3)_2$ |
| Ac | Ac | S | $CH_2CH[N(CH_3)_2]CH_3$ |
| Ac | Ac | S | $CH-[2-(CH_3)_2NH_5C_4]$ |
| Pr | H | S | $CH_2-[4-(CH_3)_2NC_6H_4]$ |
| Pr | H | S | $CH_2$-3-pyridyl |
| Ac | H | S | $CH_2$-4-pyridyl |
| Pr | H | S | $CH_2$-4-pyridyl |
| H | Ac | S | $CH_2CH_2OH$ |
| H | Ac | S | $(CH_2)_4OH$ |
| H | Ac | S | $-CH_2-[2-(CH_3)_2NH_6C_4]$ |
| H | Pr | O | $-CH_2-(4-HOC_6H_4)$ |
| H | H | S | $CH_2CH_2OH$ |
| H | H | S | $CH_2$-2-pyridyl |
| H | H | S | $CH_2-[2-(CH_3)_2NC_6H_4]$ |

Solvolysis of alkanoyl group in the 2' position (R₂) by stirring the 2'-alkanoyl compound under a nitrogen atmosphere at ambient temperature in excess methanol for 18 hours affords the corresponding compounds wherein $R_2$ is hydrogen. The products are isolated by evaporation of the methanol solution to dryness under reduced pressure.

EXAMPLE 2

11-Acetyl-4″-deoxy-4″-(ethoxycarbonyl)amino-oleandomycin

Under a nitrogen atmosphere a solution of 11-acetyl-4″-deoxy-4″-amino-oleandomycin (10 g., 13.7 mmol.) and triethylamine (3 ml.) in tetrahydrofuran (100 ml.) is stirred and cooled to −78° C. A solution of ethyl chloroformate (1.4 ml.) in tetrahydrofuran (2 ml.) is added over a period of one minute. Almost immediately a white precipitate forms but stirring is continued for a half-hour. Chloroform (50 ml.) and water (5 ml.) are added to the reaction mixture which is then stripped to leave a yellow oil. The oil is partitioned between ethyl acetate (100 ml.) and water (100 ml.) and the pH adjusted to 3.4. The ethyl acetate phase is separated and the aqueous phase extracted with fresh portions of ethyl acetate at each of pH values 5.0, 6.1, 6.4, 7.5 and 9.5. The extracts from the pH 1.6 and 6.4 extractions are combined, dried (Na₂SO₄) and evaporated to dryness to give 5.2 g. of a pale yellow foam. The foam is chromatographed on silica gel (250 g.) using acetone as eluant. Fractions of 100 ml. volume each are collected. Fraction 8-23 are combined and evaporated under reduced pressure to give a white foam (3.7 g.). It is crystallized by dissolution in a minimum volume of isopropanol (~10 ml.) and then adding water (~10 ml.) slowly with rapid stirring. The mixture is stirred until precipitation is complete and the solid then filtered and dried in a vacuum oven at room temperature to give 2.48 g. of white crystals; m.p. — softens at ~98° C., melts at 106°-108° C. (yield = 23%).

NMR (60 MHz) $\delta_{CDCl_3}^{TMS}$ (ppm): 3.43 (s, 3H), 2.66 (d, J=2, 2H), 2.32 (s, 6H), 2.08 (s, 3H).

Mass Spec. m/e = 216.

The following compounds are prepared in like manner from appropriate reactants:

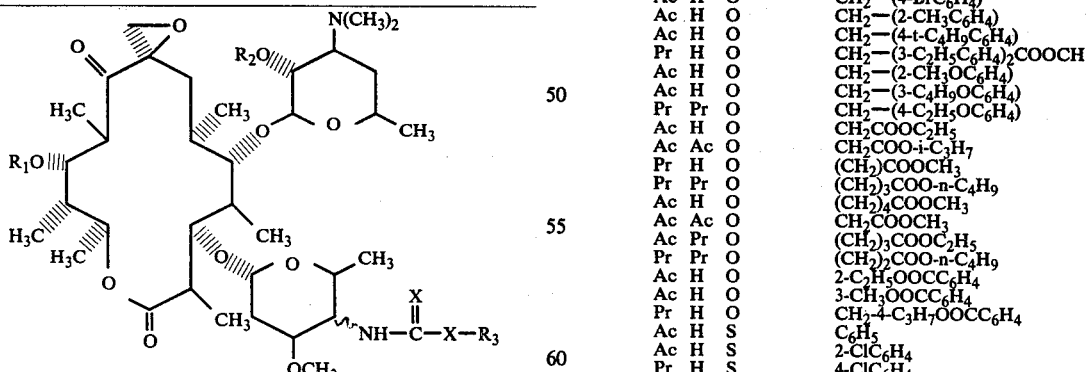

| R₁ | R₂ | X | R₃ |
|----|----|----|----|
| Ac | H | O | i-C₃H₇ |
| Ac | H | O | n-C₄H₉ |
| Ac | Ac | O | t-C₄H₉ |
| Pr | H | O | C₂H₅ |
| Ac | H | O | 2-ClC₆H₄ |
| Ac | H | S | i-C₄H₉ |
| Ac | Ac | S | sec-C₄H₉ |
| Pr | H | O | CH₂CH₂OCH₃ |

-continued

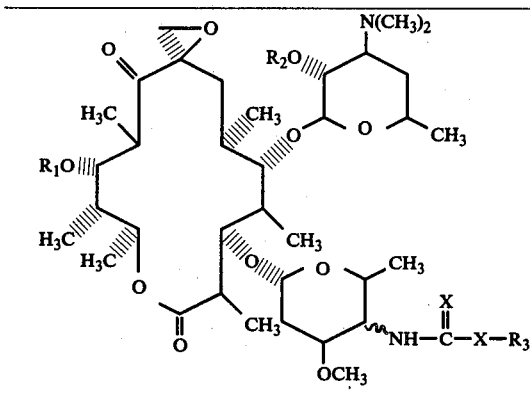

| R₁ | R₂ | X | R₃ |
|----|----|----|----|
| Ac | H | O | (CH₂)₃OC₂H₅ |
| Ac | Ac | O | (CH₂)₂—O-n-C₄H₉ |
| Pr | Pr | O | (CH₂)₄—OC₂H₅ |
| Pr | Pr | O | (CH₂)₂—O-i-C₃H₇ |
| Ac | H | O | CH₂OCH₃ |
| Ac | H | O | (CH₂)₄Cl |
| Ac | Pr | O | CH₂CH₂Br |
| Pr | H | O | (CH₂)₄Br |
| Ac | H | O | CH₂CH(Cl)CH₃ |
| Ac | H | O | CH₂CH(Cl)C₂H₅ |
| Ac | H | O | CH(CH₃)CH(Br)CH₃ |
| Ac | H | O | C(CH₃)₂CH₂Cl |
| Pr | Ac | O | CH₂—O-n-C₃H₇ |
| Ac | H | S | CH(CH₃)CH₂Br |
| Pr | H | S | CH₂CH(CH₃)Cl |
| Ac | H | S | CH₂CH(CH₃)CH₂Cl |
| Ac | Ac | S | CH(CH₃)CH₂COOCH₃ |
| Pr | H | O | C₆H₅ |
| Ac | H | O | 2-CH₃OC₆H₄ |
| Ac | Ac | O | 4-CH₃OC₆H₄ |
| Pr | Ac | O | 3-C₂H₅OC₆H₄ |
| Ac | Pr | O | 4-n-C₄H₉OC₆H₄ |
| Ac | Ac | O | 2-i-C₄H₉OC₆H₄ |
| Pr | H | O | 3-n-C₃H₇OC₆H₄ |
| Ac | Ac | O | 2-ClC₆H₄ |
| Ac | Ac | O | 4-ClC₆H₄ |
| Pr | Pr | O | 3-BrC₆H₄ |
| Ac | H | O | 3-BrC₆H₄ |
| Ac | Pr | O | 4-ClC₆H₄ |
| Pr | H | O | 4-BrC₆H₄ |
| Ac | H | O | 2-CH₃C₆H₄ |
| Ac | H | O | 4-CH₃C₆H₄ |
| Pr | Ac | O | 3-C₂H₅C₆H₄ |
| Ac | H | O | 4-t-C₄H₉C₆H₄ |
| Pr | Pr | O | 3-n-C₃H₇C₆H₄ |
| Ac | H | O | CH₂—C₆H₅ |
| Pr | H | O | CH₂—(2-ClC₆H₄) |
| Pr | Pr | O | CH₂—(4-ClC₆H₄) |
| Ac | Ac | O | CH₂—(3-ClC₆H₄) |
| Ac | H | O | CH₂—(4-BrC₆H₄) |
| Ac | H | O | CH₂—(2-CH₃C₆H₄) |
| Ac | H | O | CH₂—(4-t-C₄H₉C₆H₄) |
| Pr | H | O | CH₂—(3-C₂H₅C₆H₄)₂COOCH |
| Ac | H | O | CH₂—(2-CH₃OC₆H₄) |
| Ac | H | O | CH₂—(3-C₄H₉OC₆H₄) |
| Pr | Pr | O | CH₂—(4-C₂H₅OC₆H₄) |
| Ac | H | O | CH₂COOC₂H₅ |
| Ac | Ac | O | CH₂COO-i-C₃H₇ |
| Pr | H | O | (CH₂)COOCH₃ |
| Pr | Pr | O | (CH₂)₃COO-n-C₄H₉ |
| Ac | H | O | (CH₂)₄COOCH₃ |
| Ac | Ac | O | CH₂COOCH₃ |
| Ac | Pr | O | (CH₂)₃COOC₂H₅ |
| Pr | Pr | O | (CH₂)₂COO-n-C₄H₉ |
| Ac | H | O | 2-C₂H₅OOCC₆H₄ |
| Ac | H | O | 3-CH₃OOCC₆H₄ |
| Pr | H | O | CH₂-4-C₃H₇OOCC₆H₄ |
| Ac | H | S | C₆H₅ |
| Ac | H | S | 2-ClC₆H₄ |
| Pr | H | S | 4-ClC₆H₄ |
| Pr | H | S | 2-BrC₆H₄ |
| Pr | H | S | 3-CH₃OC₆H₄ |
| Ac | Ac | S | 4-t-C₄H₉OC₆H₄ |
| Ac | Ac | S | 2-C₂H₅OC₆H₄ |
| Ac | Pr | S | 4-CH₃C₆H₄ |
| Ac | H | S | 4-t-C₄H₉C₆H₄ |
| Pr | Pr | S | 2-C₂H₅C₆H₄ |
| Ac | H | S | CH₂CH(CH₃)CH₂OCH₃ |
| Pr | H | S | CH₂CH(CH₃)CH₂O-n-C₄H₉ |
| Ac | H | S | CH₂COOC₂H₅ |
| Ac | H | S | CH₂COOCH₃ |

-continued

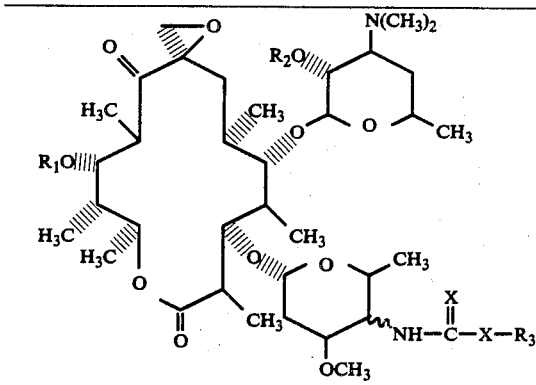

| R₁ | R₂ | X | R₃ |
|---|---|---|---|
| Pr | Pr | S | (CH₂)₃COOCH₃ |
| Pr | H | S | (CH₂)₄COO-sec-C₄H₉ |
| Ac | H | S | (CH₂)₄COOCH₃ |
| Pr | H | S | C₂H₅ |
| Ac | H | S | CH₂CH₂OCH₃ |
| Ac | Pr | S | CH₂OCH₃ |
| Ac | H | S | CH₂CH(OC₂H₅)C₂H₅ |
| Pr | Pr | S | CH₂OC₄H₉ |
| Pr | Pr | S | CH₃ |
| Ac | H | S | (CH₂)₃Cl |
| H | Ac | O | C₂H₅ |
| H | Pr | O | CH₃ |
| H | Ac | S | CH₂CH₂COO-t-C₄H₉ |
| H | Ac | S | (CH₂)₄COO-i-C₃H₇ |
| H | Pr | O | CH₂OCH₃ |
| H | Ac | O | CH₂O(n-C₄H₉) |
| H | Pr | O | C₆H₅ |
| H | Pr | S | 4-ClC₆H₄ |
| H | Ac | S | CH₃ |
| H | Ac | S | 2-BrC₆H₄ |
| H | Ac | S | 2-CH₃C₆H₄ |
| H | Ac | O | 4-t-C₄H₉C₆H₄ |
| H | Pr | O | 4-CH₃OOCC₆H₄ |
| H | Ac | S | 3-C₂H₅OC₆H₄ |
| H | Ac | S | —CH₂—(2-CH₃OOCC₆H₄) |
| H | Pr | O | —CH₂—(3-BrC₆H₄) |
| H | H | O | C₂H₅ |
| H | H | S | CH₃ |
| H | H | S | CH₂CH(OCH₃)CH₃ |
| H | H | S | CH(CH₃)CH₂Cl |
| H | H | O | CH₂—C₆H₅ |
| H | H | O | 4-CH₃OC₆H₄ |

The 2'-alkanoyl derivatives described above are transformed to the corresponding alcohols (R₂=H) by the solvolysis procedure of Example 1.

Repetition of the preceding Examples but using the appropriate reactants affords the following compounds of formula II:

perature for one hour. Removal of the solvent by evaporation affords the hydrochloride salt.

In like manner, the above-named compound and the remaining compounds described herein are converted to their hydrochloride, hydrobromide, sulfate, acetate, butyrate, citrate, glycolate, tartrate, stearate, pamoate, fumarate, benzoate and aspartate salts.

When the reactants is an 11,2'-dialkanoyl-4"-deoxy-4"-substituted amino-oleandomycin derivative, isopropanol is used as solvent.

Other acid addition salts are prepared by adding sufficient acid to satisfy each of the basic groups present. In this manner poly-acid addition salts of compounds of this invention are prepared.

PREPARATION A

11-Acetyl-4"-deoxy-4"-amino-oleandomycin

To a suspension of 10% palladium-on-charcoal (10 g.) in methanol (100 ml.) is added ammonium acetate (21.2 g.) and the resulting slurry is treated with a solution of 11-acetyl-4"-deoxy-4"-oxo-oleandomycin (20 g.) in 100 ml. of the same solvent. The suspension is shaken at room temperature in a hydrogen atmosphere at an initial pressure of 50 p.s.i. After 1.5 hours, the catalyst is filtered and the filtrate is added with stirring to a mixture of water (1200 ml.) and chloroform (500 ml.). The pH is adjusted from 6.4 to 4.5 and the organic layer is separated. The aqueous layer, after a further extraction with chloroform (500 ml.), is treated with ethyl acetate (500 ml.) and the pH adjusted to 9.5 with 1N sodium hydroxide. The ethyl acetate layer is separated and the aqueous layer extracted again with ethyl acetate. The ethyl acetate extracts are combined, dried over sodium sulfate and concentrated to a yellow foam (18.6 g.), which on crystallization from diisopropyl ether, provides 6.85 g. of the purified product, m.p. 157.5–160° C.

NMR (δ, CDCl₃): 3.41 (3H)s, 2.70 (2H)m, 2.36 (6H)s, and 2.10 (3H)s.

The other epimer, which exists in the crude foam to the extent of 20–25%, is obtained by gradual concentration and filtration of the mother liquors.

In like manner, the following mono-alkanoyl and dialkanoyl esters of 4"-deoxy-4"-amino-oleandomycin are prepared from the appropriate mono-alkanoyl and dialkanoyl 4"-deoxy-4"-oxo-oleandomycins. When a 2'-ester is prepared, isopropanol is used as solvent.

| Example | X | R₁ | R₃ | % Yield | MS (m/e) | Procedure | NMR (60 MHz) $\delta^{TMS}_{CDCl_3}$ (ppm) |
|---|---|---|---|---|---|---|---|
| 3 | S | Ac | CH₃ | 46 | | 1 | 3.47 (s,3H), 2.68 (s,broad base,5H), 2.3 (s,6H), 2.08 (s,3H). |
| 4 | S | Ac | CH₂—(2-pyridyl) | 11 | | 1 | 7.0–8.6 (m,4H), 3.51 (s,3H), 2.72 (d,J=2, 2H), 2.35 (s,6H), 2.07(s,3H). |
| 5 | S | Ac | CH₂CH₂OH | 11 | | 1 | 3.47 (s,3H), 2.67 (d,J=2,2H), 2.31(d,6H), 2.08 (s,3H). |
| 6 | O | Ac | CH₂—C₆H₅ | 19 | | 2 | 7.33 (s,5H), 5.18 (s,2H), 3.45 (s,3H), 2.66 (d,J=2,2H), 2.30 (s,6H), 2.08 (s,3H). |
| 7 | O | Ac | C₆H₅ | 16 | | 2 | 7.32 (broad,s,5H), 3.48 (s,3H), 2.68 (d,J=2, 2H), 2.32 (s,6H), 2.10 (s,3H). |
| 8 | O | H | C₂H₅ | 16 | 216 230 | 2 | 3.40 (s,3H), 2.30 (s,6H). |

EXAMPLE 9

Acid Addition Salts

To a solution of 11-acetyl-4"-deoxy-4"-ethoxycarbonylamino-oleandomycin (1.0 mmole) in methanol (50 ml.) is added an equimolar proportion of hydrogen chloride and the reaction mixture stirred at room tem-

| | |
|---|---|
| 11,2'-diacetyl- | 11-propionyl- |
| 2'-acetyl- | 11-acetyl-2-propionyl- |
| 2'-propionyl- | 11-propionyl-2-acetyl- |
| 11,2'-dipropionyl | |

PREPARATION B

4"-Deoxy-4"-amino-oleandomycin

A solution of 2'-acetyl-4"-deoxy-4"-oxo-oleandomycin (20 g.) in methanol (125 ml.), after stirring at room temperature overnight, is treated with ammonium acetate (21.2 g.). The resulting solution is cooled in an ice bath and treated with sodium cyanoborohydride (1.26 g.). The cooling bath is then removed and the reaction mixture allowed to stir at room temperature for 2 hours. The reaction is poured into water (600 ml.) and diethyl ether (600 ml.) and the pH adjusted from 8.3 to 7.5. The ether layer is separated and the aqueous phase extracted with ethyl acetate. The extracts are set aside and the pH of the aqueous adjusted to 8.25. The diethyl ether and ethyl acetate extracts made at this pH are also set aside, and the pH raised to 9.9. The diethyl ether and ethyl acetate extracts at this pH are combined, washed successively with water (1×) and a saturated brine solution and dried over sodium sulfate. The latter extracts, taken at pH 9.9, are concentrated to a foam and chromatographed on silica gel (160 g.), using chloroform as the loading solvent and initial eluate. After eleven fractions, 12 ml. per fraction are taken, the eluate is changed to 5% methanol-95% chloroform. At fraction 370 the eluate is changed to 10% methanol-90% chloroform and at fraction 440, 15%methanol-85% chloroform is used. Fractions 85–260 are combined and concentrated in vacuo to dryness to provide 2.44 g. of the desired product.

NMR ($\epsilon$, CDCl$_3$): 5.56 (1H) m, 3.36 (3H) s, 2.9 (2H) m, and 2.26 (6H)s.

What is claimed is:

1. A compound having the formula:

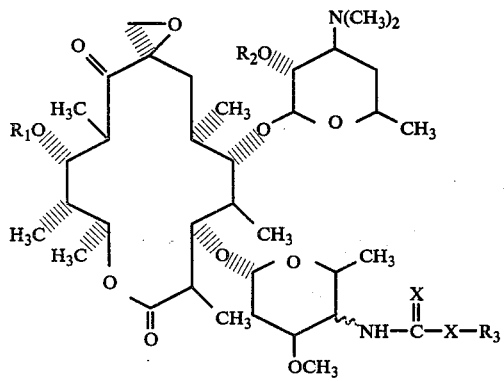

and the pharmaceutically acceptable salts thereof wherein
each of R$_1$ and R$_2$ is selected from the group consisting of hydrogen and alkanoyl having from two to three carbon atoms;
X is selected from the group consisting of O and S;
R$_3$ is selected from the group consisting of (i) a first subgroup consisting of:

—(C$_n$H$_{2n}$)—Z$_1$ wherein Z$_1$ is selected from the group consisting of hydrogen, chloro, bromo, carboalkoxy having from one to four carbon atoms in the alkoxy group, hydroxy, alkoxy having from one to four carbon atoms and dimethylamino;
and n is an integer from 1 to 4; with the provisos that each Z$_1$ is hydroxy, chloro, bromo or dimethylamino, n is an integer from 2 to 4; and when X is O, Z$_1$ is other than hydroxy or dimethylamino;
(ii) a second subgroup consisting of:

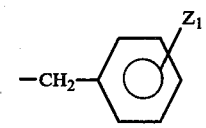

wherein Z$_1$ is as defined above.
(iii) a third subgroup consisting of:

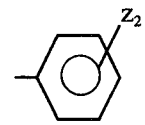

wherein Z$_2$ is selected from the group consisting of hydrogen, chloro, bromo, carboalkoxy having from one to four carbon atoms in the alkoxy group, alkoxy having from one to four carbon atoms and alkyl having from one to four carbon atoms; and, when X is S,
(iv) a fourth subgroup consisting of:

—CH$_2$—pyridyl.

2. A compound according to claim 1 wherein R$_1$ is alkanoyl, R$_2$ is hydrogen and R$_3$ is —(C$_n$H$_{2n}$)—Z$_1$.

3. A compound according to claim 2 wherein R$_1$ is acetyl and Z$_1$ is hydrogen.

4. The compound according to claim 3 wherein X is O and n is 2.

5. The compound according to claim 3 wherein X is S and n is 1.

6. A compound according to claim 2 wherein R$_1$ is acetyl and Z$_1$ is hydroxy.

7. The compound according to claim 6 wherein X is S and n is 2.

8. A compound according to claim 1 wherein R$_1$ is alkanoyl, R$_2$ is hydrogen and R$_3$ is

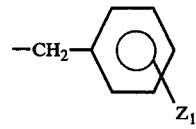

9. The compound according to claim 8 wherein X is O and Z$_1$ is hydrogen.

10. A compound according to claim 1 wherein R$_1$ is alkanoyl, R$_2$ is hydrogen and R$_3$ is —CH$_2$—pyridyl.

11. The compound according to claim 10 wherein X is S and R$_3$ is —CH$_2$—(2-pyridyl).

* * * * *

UNITED STATES PATENT OFFICE
CERTIFICATE OF CORRECTION

PATENT NO. : 4,133,950
DATED : January 9, 1979
INVENTOR(S) : Robert F. Myers

It is certified that error appears in the above-identified patent and that said Letters Patent are hereby corrected as shown below:

Col. 2, line 63, "but are limited" should read -- but not limited --

Col. 2, line 66, "tartrate, maleate," should read -- tartrate, malate, maleate, --.

Signed and Sealed this

First Day of May 1979

[SEAL]

Attest:

RUTH C. MASON
Attesting Officer

DONALD W. BANNER
Commissioner of Patents and Trademarks